Figure 1:
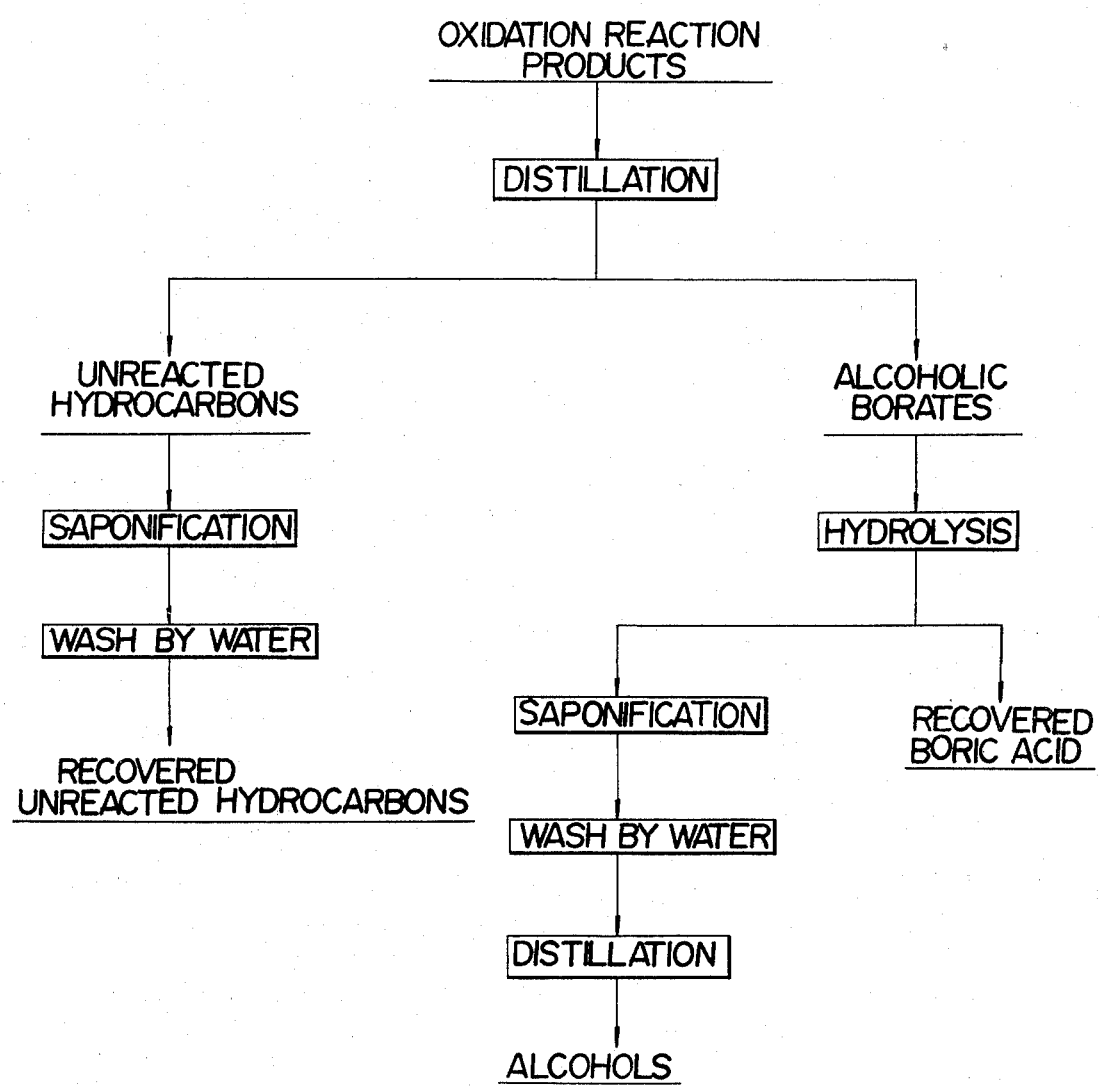

United States Patent [19]
Fujii et al.

[11] 3,989,763
[45] Nov. 2, 1976

[54] METHOD FOR RECOVERING ALCOHOLS

[75] Inventors: Toshihiro Fujii, Neyagawa; Naoji Kurata, Nichinomiya; Yukio Okuda, Toyonaka, all of Japan

[73] Assignee: Nippon Shokubai Kagaku Kogyo Co., Ltd., Osaka, Japan

[22] Filed: Sept. 20, 1974

[21] Appl. No.: 507,885

Related U.S. Application Data

[63] Continuation of Ser. No. 219,789, Jan. 21, 1972, abandoned, which is a continuation-in-part of Ser. No. 816,326, April 15, 1969, abandoned.

[30] Foreign Application Priority Data
Apr. 17, 1968   Japan .............................. 43-25230

[52] U.S. Cl. ..................... 260/643 A; 260/639 B
[51] Int. Cl.$^2$ ...................................... C07C 29/24
[58] Field of Search .................. 260/639 B, 643 A

[56] References Cited
UNITED STATES PATENTS

| | | | |
|---|---|---|---|
| 2,587,753 | 3/1952 | O'Conner et al. | 260/643 A |
| 2,626,284 | 1/1953 | Smith | 260/643 E |
| 3,188,354 | 6/1965 | Roming | 260/643 A |
| 3,410,913 | 11/1968 | McMahon et al. | 260/639 B |
| 3,420,897 | 1/1969 | Russell et al. | 260/639 B |
| 3,442,959 | 5/1969 | Sugerman | 260/639 B |
| 3,524,891 | 8/1970 | Cahn | 260/639 B |
| 3,524,893 | 8/1970 | Doyle et al. | 260/639 B |
| 3,683,035 | 8/1972 | Alagy et al. | 260/639 B |

*Primary Examiner*—Joseph E. Evans
*Attorney, Agent, or Firm*—Sherman & Shalloway

[57] ABSTRACT

A process for the preparation of alcohols by oxidizing aliphatic saturated hydrocarbons, having 10–20 carbon atoms, in the presence of a boron compound, contacting the oxidation reaction mixture with water, removing the aqueous solution of boric acid, and separating the resulting oil layer with saponification and washing with water. A boron compound is added to the resulting oil layer to esterify the alcohols therein. The resulting mixture is distilled to remove unreacted hydrocarbons, the residue comprising borate esters of alcohols is contacted with water, the aqueous solution of boric acid is removed, and the resulting oil layer is separated and distilled to recover the desired alcohols.

9 Claims, 2 Drawing Figures

METHOD FOR RECOVERING ALCOHOLS

This is a continuation of application Ser. No. 219,789, filed Jan. 21, 1972, now abandoned which is, in itself, a continuation-in-part of application Ser. No. 816,326, filed Apr. 15, 1969, now abandoned.

This invention relates to a method for the recovery of alcohols. More specifically, this invention relates to an improved process involving saponification prior to the distillation to recover unreacted hydrocarbons from a reaction mixture obtained by the liquid phase oxidation of aliphatic saturated hydrocarbons with a gas containing molecular oxygen in the presence of a boron compound.

Prior to the present invention it has been known to produce alcohols by the liquid phase oxidation of aliphatic saturated hydrocarbons with a gas containing molecular oxygen in the presence of a boron compound, such as boric acid, meta-boric acid, boric anhydride and borate esters as a catalyst. These alcohols are used, for instance, as surface active agents after ethoxylation and/or sulfation. In such reaction, the boron compound converts the resulting alcohols to their borate esters thereby stabilizing them. The presence of the boron compound is therefore to prevent the alcohols from being consecutively oxidized and to facilitate removal of unreacted hydrocarbons from the reaction mixture by distillation.

A Conventional process will be described by reference to FIG. 1 which is a simplified flowsheet thereof. Aliphatic saturated hydrocarbons are subjected to liquid phase oxidation with a gas containing molecular oxygen in the presence of a boron compound. The resulting oxidation reaction mixture is separated by distillation into the distillate comprising unreacted hydrocarbons and volatile byproducts, such as carbonyl compounds, carboxylic acids, carboxylic esters, lactones, and unsaturated hydrocarbons, and the residue comprising borate esters of alcohols. The distillate is purified by removing such compounds as carboxylic acids, carboxylic esters and lactones by saponification with, for instance, sodium hydroxide and washing with water and thereafter recycled to the oxidation process. The residue separated by distillation is contacted with water to hydrolyze the borate esters. The resulting oil layer is saponified, washed with water, and fractionally distilled to obtain the purified alcohols. The boric acid is recovered from the aqueous layer.

While such method has been disclosed in the literature the alcohols obtained by such method are colored yellow and have offensive odors resulting from impurities, posing a considerable problem of quality in using them as surface active agents or for cosmetics. Various methods have therefore been proposed to purify the alcohols produced in such a manner; however, none of such methods has yet been satisfactory, or economically advantageous.

Research has been conducted to determine the causes of such coloration and offensive odors with a view to preparing alcohols free from color and offensive odor ascribable to impurities. Such research led to the accomplishment of the present invention.

The reaction mixture obtained by liquid phase oxidation of aliphatic saturated hydrocarbons with a gas containing molecular oxygen in the presence of a boron compound, comprises borate esters of the desired alcohols and unreacted hydrocarbons. The mixture also contains impurities formed during the oxidation reaction, such as carbonyl compounds, carboxylic acids, carboxylic esters, lactones and unsaturated compounds. The volatile compounds amoung them may be removed from the residue together with the unreacted hydrocarbons.

This concept, "boration process", has been taught by O'Connor et al U.S. Pat. No. 2,587,753, Roming U.S. Pat. No. 3,188,354, Sugerman U.S. Pat. No. 3,442,959, Fetterly et al U.S. Pat. No. 3,375,265, and other literature references.

On the other hand, the impurities having higher boiling points remaining in the residue, such as carboxylic acids, carboxylic esters, lactones and the like, may be almost entirely removed in the subsequent saponification and water washing steps of the hydrolyzed oil layer.

In spite of these facts, when aliphatic saturated hydrocarbons having 10–20 carbons atoms are used as in the case of present invention, the resulting alcohols are still colored yellow, and have objectionable odors ascribable to impurities. It is therefore presumed from this fact that impurities which cause coloration and objectionable odor will also be formed in the distillation step of the oxidation reaction mixture.

It has now been found that a portion of the impurities in the products will decompose because of the high temperature during the distillation of the reaction mixture; that these impurities and their decomposed products may decompose or react with a portion of the borate esters of alcohols to form new unknown substances, and cause coloration and offensive odors; and that the newly formed impurities may remain unremoved in the alcohols which are obtained.

Accordingly it has been found that if the impurities in the products are removed by the saponification prior to the recovery of the unreacted hydrocarbons from the oxidation reaction mixture by distillation, the desired alcohols contain no unknown impurities and become free from color and offensive odors. Such effects are truly unexpected from that which is already known in the literature.

Specifically, the oxidation reaction mixture is immediately contacted with water, removing the aqueous solution of boric acid, and the resulting oil layer is separated. Similar treatment has also been taught by Russell et al U.S. Pat. No. 3,420,897 in the case of the oxidation reaction mixture of cyclohexane.

In the case of the present invention, this watercontacting step of the oxidation reaction mixture is merely accomplished by a usual method, prior to the subsequent saponification step, removing the aqueous solution of boric acid. Such operation is usually done to prevent undesirable loss of boric acid and alkali in the saponification step.

The resulting oil layer is then subjected to the "saponification", the most important step of the present invention, followed by a water-washing step. In these steps the impurities formed during the oxidation, such as carboxylic acids, carboxylic esters, lactones and the like, are removed almost entirely without causing the formation of unknown compounds, the source of undesirable color and odor. Then such compounds as boric acid, metaboric acid, boric anhydride and borate esters are added to the water-washed oil layer mainly comprising unreacted hydrocarbons and alcohols, and the mixture is subjected to esterification. Unreacted hydrocarbons and volatile byproducts are then recovered by distillation and the distillate is returned to the oxidation step. The residue mainly comprising borate esters of alcohols is contacted with water, removing the aqueous solution of boric acid. Thereafter, the oil layer is distilled to thereby yield high purity alcohols free from color and offensive odors ascribable to impurities.

Figure 2:
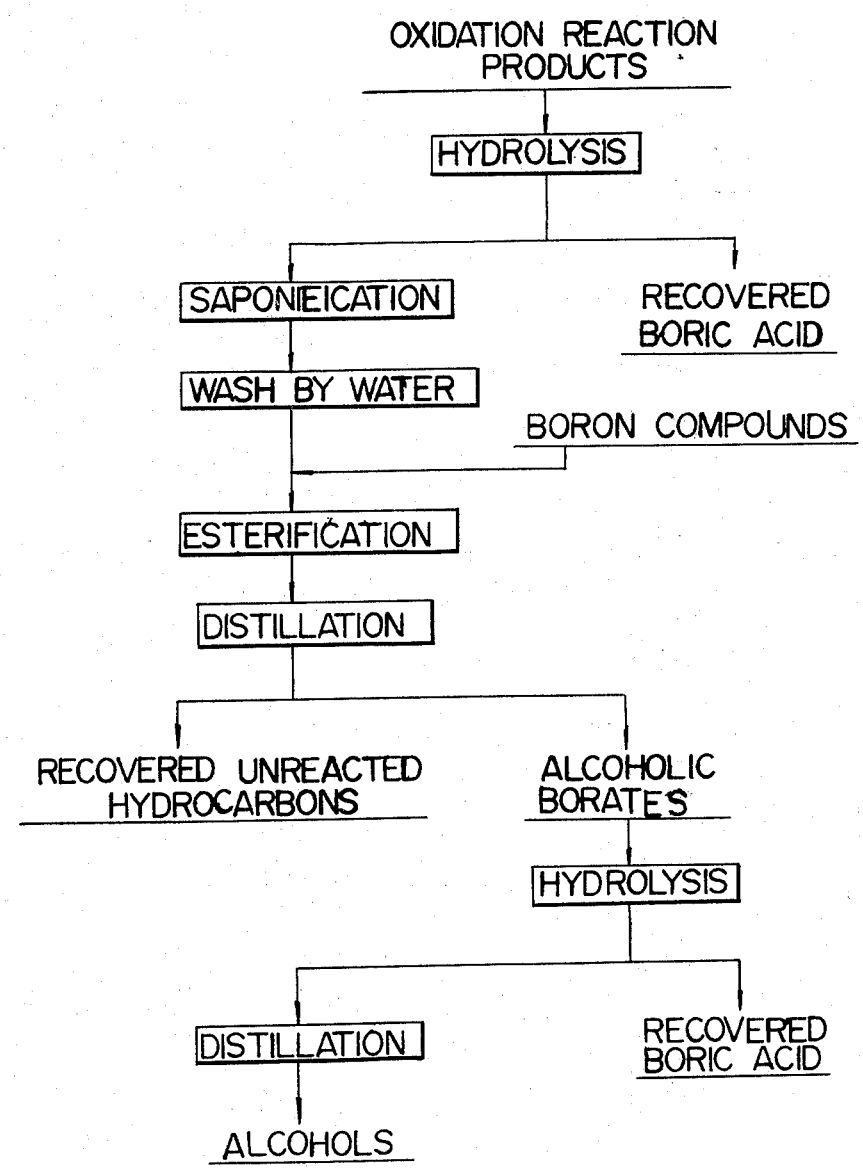

FIG. 2 illustrates the process of the present invention in a simplified manner and the process of this invention will be described in detail with reference to FIG. 2 as follows. An aliphatic saturated hydrocarbon is subjected to liquid phase oxidation with a gas containing molecular oxygen in the presence of a boron compound. The reaction mixture is contacted with water in an amount sufficient to hydrolyze the borate esters of the alcohols formed. The hydrolysis is usually carried out at a temperature within the vicinity of 100° C., but depending upon the case of hydrolysis of the borate esters of the alcohols, the hydrolysis can be carried out at temperatures below such temperature, or at high temperatures and elevated pressures. After the hydrolysis step is carried out by batchwise or countercurrent method, the aqueous solution of boric acid is separated from the oil layer and boric acid is recovered by conventional techniques.

The oil layer after removal of boric acid is saponified with alkali, followed by washing with water to remove the carboxylic acids, carboxylic esters, lactones, etc, occuring as impurities. Sodium hydroxide, potassium hydroxide and other alkalis can be used as the alkali in the saponification but the use of sodium hydroxide is economically most advantageous. The saponification should be carried out at a temperature of 50°–200° C., preferably at 100°–150° C., using an alkali in an amount at least theoretically sufficient to lower the saponification value of the resulting oil layer to zero. The pressure, the time period, the number of times, and the concentration of alkali in the aqueous solution of the saponification procedure may be appropriately chosen in order to remove these fatty acids, esters and lactones, etc. and accomplish the above object. The saponification and subsequent washing may be carried out by a batchwise or counter-current method.

The boric acid and impurities occurring as by-products are removed as much as possible by the above-mentioned steps. Thereafter, a boron compound such as boric acid, meta-boric acid, boric anhydride and borate esters is added to the oil layer, followed by heating so as to thereby convert the alcohols in the oil layer into the corresponding borates. Subsequently, the unreacted hydrocarbon and a small amount of volatile byproducts comprising carbonyl compounds and unsaturated hydrocarbons, are distilled off from the resulting esterification mixture. If necessary, the distillate is recycled to the oxidation step without further treatment. The amount of the boron compound used to esterify the alcohols must be sufficient to complete the esterification and form the alcohols into their complete borates when the unreacted hydrocarbon is distilled off after conversion of the alcohols into their borates. Conversion of the alcohols into their borates is generally carried out at a temperature of 100°–150° C. for a period of 0.5 to 3 hours although the time and temperature may vary depending upon the desired alcohols. Also, it is preferable to effect the conversion of alcohols into their borates in an atmosphere of an inert gas such as nitrogen. The esterification time may be shortened by utilizing an azeotrope with a suitable inert solvent or by entrainment by an inert gas such as nitrogen or by treating at reduced pressure, whereby the water generated by the esterification or alcohols of lower molecular weight formed in a free state by an ester-interchange reaction can be removed from the system with good efficiency. If it is possible to select conditions such as to complete conversion to borate esters without distilling out the desired alcohols while distilling the unreacted hydrocarbon, it is not necessary to provide a step of converting the alcohols into their borates.

The residue which mainly comprises the borate esters of the alcohols is then contacted with water under suitable conditions with a suitable amount of water to thereby remove boric acid and recover the oil layer. The oil layer which is recoved contains monohydric alcohols and minor amounts of polyhydric alcohols. Alcohols free from color and odor can be obtained by distilling the oil layer.

The process of the present invention does not necessitate a step of treating the recovered unreacted hydrocarbon, a step of treating the resulting alcohols, and a step of redistillation which are essential to the conventional processes heretofore known. Furthermore, the quality of the recovered hydrocarbon is better than that in the conventional processes. The amount of impurities involved in the final alcohols obtained according to the present invention is less than that in the purified alcohols obtained by conventional processes. The quality of the product according to the present invention is excellent and is commercially very advantageous.

The process of the invention is applicable to the manufacture of alcohols by liquid phase oxidation of aliphatic saturated hydrocarbons having 10–20 carbon atoms with a gas containing molecular oxygen in the presence of a boron compound. Suitable saturated hydrocarbons having 10–20 carbon atoms include, for example, decane, undecane, dodecane, tridecane, tetradecane, pentadecane, hexadecane, heptadecane, octadecane, nonadecane, eicosane and mixtures thereof, etc. There are various boron compounds used as catalysts for the oxidation of hydrocarbons or as esterifying agents to convert alcohols into borates. Some examples of these are orthoboric acid, meta-boric acid, boric anhydride, and borate esters. When these boron compounds are used as oxidation catalysts, an ammoniacal base can be used together with the same as a promoter.

The process of the invention will be further illustrated by the following Example and comparative examples, but it should be noted that the same are not in any way meant to limit the process of the present invention. In the following examples, description will be directed to the alcohols obtained by the oxidation of hydrocarbons having 12–14 carbon atoms, since these alcohols have little odors inherent to monohydric alcohols but they produce sharp offensive odors even if a small amount of impurities is present.

EXAMPLE

A reactor was charged with 1000g. of a mixed n-paraffin having an average molecular weight of 185 and 12–14 carbon atoms and 28g. of an anhydrous boric acid of 98.5% purity. A gaseous mixture consisting of 5% of oxygen, 95% of nitrogen and 100ppm of ammonia was introduced thereinto at a rate of 10 liters per minute, and the reaction was conducted for 2 hours at 175° C. Some 340 ml. of water were added to the oxidation reaction mixture and while stirring, the mixture was maintained for one hour at 100°–105° C. Thereafter, the aqueous layer was separated, and the residual oil layer was washed once with the same amount of water and the water layer was separated. The analysis of the oil layer which was obtained showed that the oil had an acid value of 2.2, a saponification value of 8.2 and a hydroxyl value of 67.0.

Then 340 ml. of 4% sodium hydroxide aqueous solution were added to the oil layer and while stirring, the mixture was maintained for 1.5 hours at a temperature of 100°–105° C. The aqueous layer was removed, and the oil layer was washed twice with the same amount of water. The analysis of the oil layer at this time showed an acid value of 0.0, the saponification value of 1.0 and the hydroxyl value of 68.7. Then 60g. of boric acid ($H_3BO_3$) were added to the oil layer and the mixture was stirred. While introducing nitrogen gas, the mixture was maintained for 1 hour at a temperature of 140°–150° C. The oil layer distilled out during the esterification reaction was returned to a stirring vessel, and the water formed by the reaction was removed. Thereafter, the mixture was transferred into a distillation still, and distilled until the pressure and the temperature of the distillation still reached 5 torr and 200° C. respectively, thereby removing the unreacted paraffin and a small amount of volatile byproducts as completely as possible. The results of the distillate are shown in Table 1. The distillate was found to be good enough to be recycled to the oxidation step without further treatment.

TABLE 1

| Hydroxyl value | 0.0 |
|---|---|
| Acid value | 0.0 |
| Saponification | 0.0 |
| Carbonyl value | 8.5 |
| Iodine value | 0.2 |

Some 400 ml. of water were then added to the residue consisting of boric acid esters of alcohols and a small amount of impurities and while stirring, the mixture was maintained for 1 hour at about 100° C. Thereafter, the aqueous layer was separated off and the mixture was washed once with the same amount of water. The oil layer obtained was analyzed by means of chemical analysis, infrared spectrum or gas-chromatography, and was found to contain mono-hydric secondary alcohols having 12–14 carbon atoms as main products, minor amounts of di- and polyhydric alcohols, and traces of unreacted n-paraffins and carbonyl compounds.

The oil layer was transferred into a distillation still with a packed column and was fractionally distilled at a pressure of 5 torr. The first fraction consisted of monohydric alcohols, n-paraffins and carbonyl compounds. The second fraction consisted of monohydric alcohols and traces of carbonyl compounds. The third fraction consisted of dihydric alcohols and small amounts of others. The residue was a mixture of polyhydric alcohols and resinous high boiling materials. The results of the fractional distillation and analysis of the distillates are shown in Table 2.

The determination of the rank of odor was conducted by five experts familiar with such odors by using mixtures of a crude alcohol obtained in the preparation step of the conventional process and a completely purified odor-free n-tridecane in the proportions indicated in Table 3 as standard samples.

Table 3

| | Rank of odors | 0 | 1 | 2 | 3 | 4 | 5* |
|---|---|---|---|---|---|---|---|
| Proportion (wt.%) | Crude alcohols obtained by the conventional process | 0 | 2 | 5 | 15 | 100 | |
| | Purified n-tridecane | 100 | 98 | 95 | 85 | 0 | |

*more strongly offensive odors.

The comparison of odors was determined in the same manner also in the following Comparative Examples.

COMPARATIVE EXAMPLE 1

The oxidation reaction mixture obtained by using the same starting materials and under the same conditions as in the above Example was immediately subjected to flash distillation at a pressure of 5 torr and a temperature of 200° C. to remove the unreacted n-paraffins and volatile byproducts. The results of analysis of the distillate are shown in Table 4. The distillate was not found to be good enough to be recycled to the oxidation step without further treatment.

Table 4

| Hydroxyl value | 1.7 |
|---|---|
| Acid value | 2.2 |
| Saponification value | 9.3 |
| Carbonyl value | 12.8 |
| Iodine value | 1.2 |

Then 400 ml. of water were added to the residue and while stirring, the mixture was maintained for 1 hour at 100°–105° C. Thereafter, the aqueous layer was separated, and the oil layer was washed once with the same amount of water.

Then 80 ml. of 10% aqueous solution of sodium hydroxide were added to the resulting oil layer, and while stirring, the mixture was maintained for 1.5 hours at a temperature of 100°–105° C. Thereafter, the aqueous layer was removed and the oil layer was washed twice with the same amount of water. The resulting oil layer was fractionally distilled using the same apparatus as Table 2

| | Distillation temperature (° C.) (5 mmHg) | Distillation yield (wt. %) | Hydroxyl value | Carbonyl value | Iodine value | Ratio of unreacted paraffin (wt. %) | Hazen number | Rank of Odors |
|---|---|---|---|---|---|---|---|---|
| 1st fraction | 95 – 120 | 2.1 | 228 | 2.5 | 6.8 | 20 | 10 | 2 |
| 2nd fraction | 120 – 155 | 78.3 | 279 | 0.6 | 1.6 | 0.0 | less than 5 | 1 |
| 3rd fraction | 155 – 172 | 14.7 | 436 | 8.2 | 10.1 | 0.0 | 30 | 3 |
| Residue | | 4.9 | | | | 0.0 | | | used in the above example.

The results are shown in Table 5. Even the main product (the second fraction) had a undesirable color and odor.

COMPARATIVE EXAMPLE 2

The second fraction obtained in Comparative Example 1 (in Table 5) was re-distilled at 5 torr using the same apparatus as used in above example. The results obtained are shown in Table 6. Even the main fraction had an undesirable color and odor.

Table 5

| | Distillation temperature (° C.) (5 mmHg) | Distillation yield (wt. %) | Hydroxyl value | Carbonyl value | Iodine value | Ratio of unreacted paraffin (wt. %) | Hazen number | Rank of odors |
|---|---|---|---|---|---|---|---|---|
| 1st fraction | 95 – 120 | 4.2 | 174 | 8.8 | 8.5 | 31 | 200 | 5 |
| 2nd fraction | 120 – 155 | 77.3 | 271 | 4.6 | 2.3 | 0.2 | 160 | 4 |
| 3rd fraction | 155 – 172 | 9.2 | 383 | 8.7 | 9.2 | 0.0 | 350 | 5 |
| Residue | | 9.3 | | | | 0.0 | | |

Table 6

| | Distillation temperature (° C.) (5 mmHg) | Distillation yield (wt. %) | Hydroxyl value | Carbonyl value | Iodine value | Ratio of unreacted paraffin (wt. %) | Hazen number | Rank of Odors |
|---|---|---|---|---|---|---|---|---|
| 1st fraction | less than 120 | 1.8 | 248 | 6.4 | 3.0 | 10 | 180 | 5 |
| Main fraction | 120 – 155 | 96.1 | 276 | 3.8 | 2.2 | 0.0 | 120 | 3 |
| Residue | | 2.1 | | | | 0.0 | | |

COMPARATIVE EXAMPLE 3

The example was repeated in the same manner except that the saponification period was 30 minutes. The analysis of the oil layer obtained after the saponification and the water-washing showed and acid value of 0.0, a saponification value of 2.0 and a hydroxyl value of 68.5. The subsequent treatment was also the same as in the above Example.

The results are shown in Table 7. Even the main fraction had an undesirable color and odor.

Table 7

| | Distillation temperature (° C.) (5 mmHg) | Distillation yield (wt. %) | Hydroxyl value | Carbonyl value | Iodine value | Ratio of unreacted paraffin (wt. %) | Hazen number | Rank of Odors |
|---|---|---|---|---|---|---|---|---|
| 1st fraction | 95 –120 | 2.1 | 228 | 2.6 | 6.9 | 20 | 20 | 3 |
| 2nd fraction | 120 – 155 | 78.1 | 279 | 0.6 | 1.7 | 0.0 | 10 | 2 |
| 3rd fraction | 155 – 172 | 14.8 | 434 | 8.4 | 10.5 | 0.0 | 50 | 4 |
| Residue | | 5.0 | | | | 0.0 | | |

The results of analysis of the distillate of the flash distillation are shown in Table 8. The distillate can be recycled to the oxidation step without further treatment.

Table 8

| | |
|---|---|
| Hydroxyl value | 0.0 |
| Acid value | 0.0 |
| Saponification value | 0.2 |
| Carbonyl value | 8.8 |
| Iodine value | 0.5 |

What is claimed is:

1. A process for the recovery of alcohols from a mixture produced by the liquid phase oxidation of mixed aliphatic saturated hydrocarbons having 10 to 20 carbon atoms with a gas containing molecular oxygen in the presence of a boron compound selected from the group consisting of ortho-boric acid, meta-boric acid, boric anhydride, and boric esters, comprising the steps of:
    1. immediately contacting the mixture with sufficient water to hydrolyze the borate esters of the alcohols formed at a temperature in the vicinity of 100° C., separating the resulting oil layer from the aqueous layer, and removing the resulting aqueous layer containing boric acid;
    2. saponifying the oil layer of step (1) with an alkali, at a temperature in the range of from 100° to 200° C. and a pressure of at least one atmosphere, to decrease the saponification value to less than one, and water-washing the oil layer;
    3. adding a sufficient amount of a boron compound selected from the group consisting of ortho-boric acid, meta-boric acid, and boric anhydride, to the resulting oil layer and heating the resulting mixture at a temperature of from 100° to 150° C. for a period of from 0.5 to 3 hours, to convert all alcohols therein into their borates;
    4. distilling the resulting mixture of step (3) to separate predominantly unreacted hydrocarbons from the residue;
    5. contacting the residue of step (4) with water, at about 100° C. and for about 1 hour, separating the aqueous layer to remove the resulting boric acid from the oil layer, and water-washing the oil layer; and
    6. fractionally distilling the oil layer obtained in step (5) to recover the desired alcohols.

2. The process of claim 1 wherein the alkali utilized in the saponification step (2) is sodium hydroxide.

3. The process of claim 1 wherein the temperature of step (1) is from 100° to 105° C.

4. The process of claim 1 wherein the temperature of saponification step (2) is from 100° to 105° C.

5. The process of claim 4 wherein the temperature of saponification step (2) is maintained for 1.5 hours.

6. The process of claim 1 wherein the temperature of step (3) is from 140° to 150° c.

7. The process of claim 6 wherein the temperature of step (3) is maintained for 1 hour.

8. The process of claim 1 wherein the distillation of step (4) is conducted at 5 mmHg and 200° C.

9. The process of claim 1 wherein the mixed aliphatic saturated hydrocarbons have from 12 to 14 carbon atoms.

* * * * *